(12) United States Patent
Kasirye

(10) Patent No.: US 10,624,778 B2
(45) Date of Patent: Apr. 21, 2020

(54) UNDERGARMENT HAVING URINE-COLLECTION SYSTEM

(71) Applicant: Annet Kasirye, Lowell, MA (US)

(72) Inventor: Annet Kasirye, Lowell, MA (US)

( * ) Notice: Subject to any disclaimer, the term of this patent is extended or adjusted under 35 U.S.C. 154(b) by 579 days.

(21) Appl. No.: 15/451,876

(22) Filed: Mar. 7, 2017

(65) Prior Publication Data
US 2018/0256384 A1 Sep. 13, 2018

(51) Int. Cl.
*A61M 5/32* (2006.01)
*A61F 5/44* (2006.01)
*A61B 10/00* (2006.01)
*A61F 5/451* (2006.01)
*A61F 5/453* (2006.01)
*A61F 5/449* (2006.01)
*A61F 5/442* (2006.01)
*A61F 13/49* (2006.01)
*A61F 13/496* (2006.01)
*A61M 25/00* (2006.01)
*A61M 27/00* (2006.01)
*B65D 83/10* (2006.01)
*B65D 81/02* (2006.01)

(52) U.S. Cl.
CPC .......... *A61F 5/4408* (2013.01); *A61B 10/007* (2013.01); *A61F 5/442* (2013.01); *A61F 5/449* (2013.01); *A61F 5/451* (2013.01); *A61F 5/453* (2013.01); *A61F 13/49012* (2013.01); *A61F 13/49014* (2013.01); *A61F 13/4963* (2013.01); *A61M 25/0017* (2013.01)

(58) Field of Classification Search
CPC .......... A61M 5/32; A61M 27/00; A61F 5/44; B65D 83/10; B65D 81/02
See application file for complete search history.

(56) References Cited

U.S. PATENT DOCUMENTS

| 2,944,551 | A | * | 7/1960 | Breer | A61F 5/455 604/73 |
| 4,846,816 | A | * | 7/1989 | Manfredi | A61F 5/4405 604/323 |
| 4,994,051 | A | * | 2/1991 | Walsh | A61F 5/453 604/349 |
| 7,077,833 | B2 | | 7/2006 | Bonham | |
| 7,658,730 | B2 | | 2/2010 | Conley | |
| D693,464 | S | | 11/2013 | Neely | |

(Continued)

FOREIGN PATENT DOCUMENTS

WO 2006020074 A2 2/2006

*Primary Examiner* — Tatyana Zalukaeva
*Assistant Examiner* — Ilya Y Treyger

(57) ABSTRACT

The undergarment having urine-collection system is an external catheter apparatus. The undergarment having urine-collection system is adapted for use with a patient. The undergarment having urine-collection system is an undergarment that is formed with an elastic sheeting. The elastic sheeting is a water impermeable sheeting that collects urine as it is excreted and routes the collected urine to a catheter bag. The undergarment having urine-collection system is worn in the same manner as loin wear would be worn. The undergarment having urine-collection system comprises an undergarment, a tube, and a catheter bag. The tube provides a fluidic connection between the undergarment and the catheter bag.

17 Claims, 5 Drawing Sheets

(56) References Cited

U.S. PATENT DOCUMENTS

| | | | |
|---|---|---|---|
| 8,601,615 B2* | 12/2013 | Isaacson | ............. A41F 17/00 2/400 |
| 2002/0026161 A1 | 2/2002 | Grundke | |
| 2008/0051742 A1 | 2/2008 | Ingram-Campbell | |
| 2011/0028944 A1 | 2/2011 | Hung | |
| 2011/0152802 A1 | 6/2011 | DiCamillo | |

* cited by examiner

UNDERGARMENT HAVING URINE-COLLECTION SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary sciences including orthopedic device methods or devices of non-surgical treatments, more specifically, a device worn by a patient for the reception of urine.

SUMMARY OF INVENTION

The undergarment having system is an external catheter apparatus. The undergarment having urine-collection system is adapted for use with a patient. The undergarment having urine-collection system is an undergarment that is formed with an elastic sheeting. The elastic sheeting is a water impermeable sheeting that collects urine as it is excreted and routes the collected urine to a catheter bag. The undergarment having urine-collection system is worn in the same manner as loin wear would be worn. The undergarment having urine-collection system comprises an undergarment, a tube, and a catheter bag. The tube provides a fluidic connection between the undergarment and the catheter bag.

These together with additional objects, features and advantages of the undergarment having urine-collection system will be readily apparent to those of ordinary skill in the art upon reading the following detailed description of the presently preferred, but nonetheless illustrative, embodiments when taken in conjunction with the accompanying drawings.

In this respect, before explaining the current embodiments of the undergarment having urine-collection system in detail, it is to be understood that the undergarment having urine-collection system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the undergarment having urine-collection system.

It is therefore important that the claims be regarded as including such equivalent construction insofar as they do not depart from the spirit and scope of the undergarment having urine-collection system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
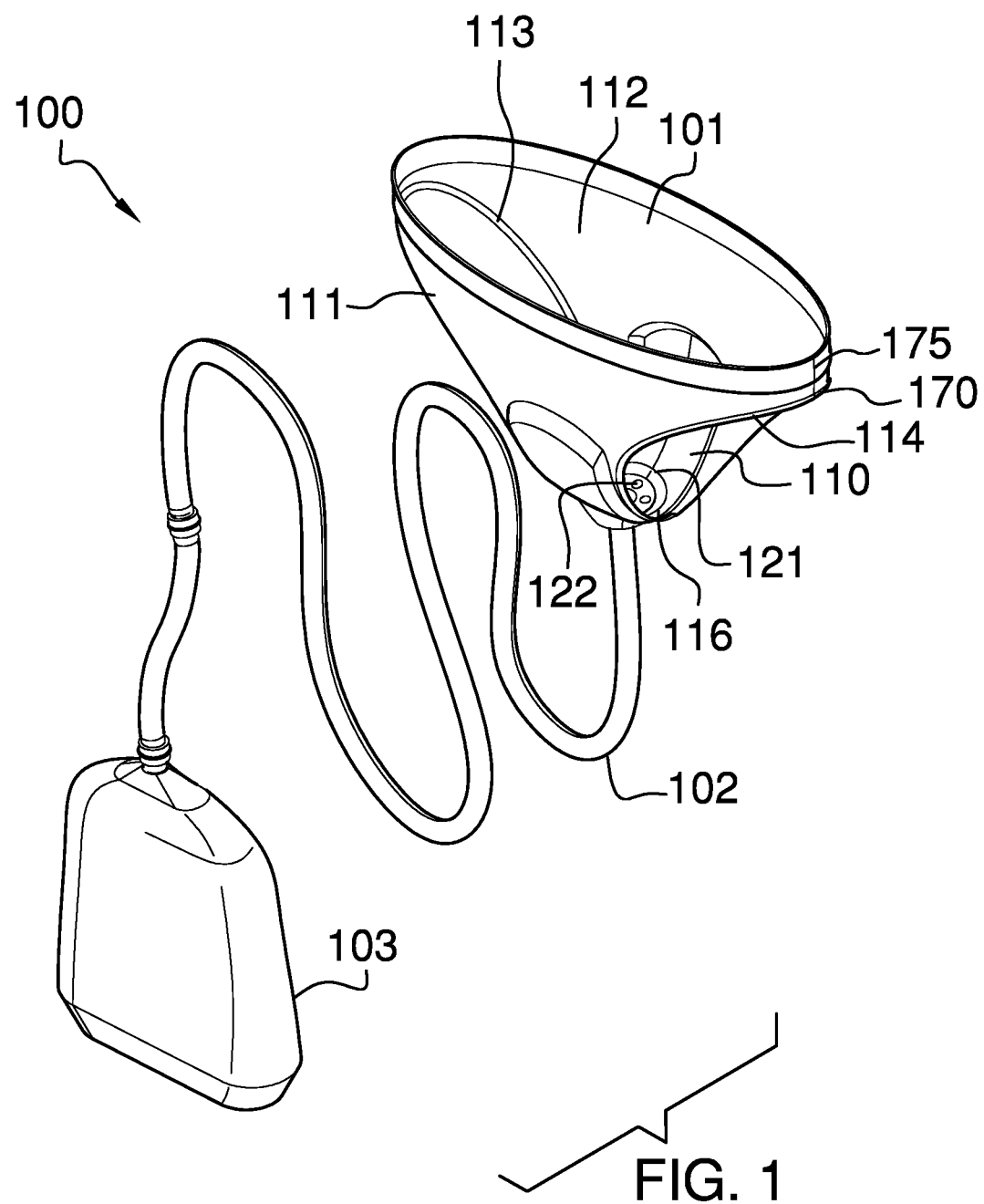
FIG. 1 is a perspective view of an embodiment of the disclosure.
Figure 2:
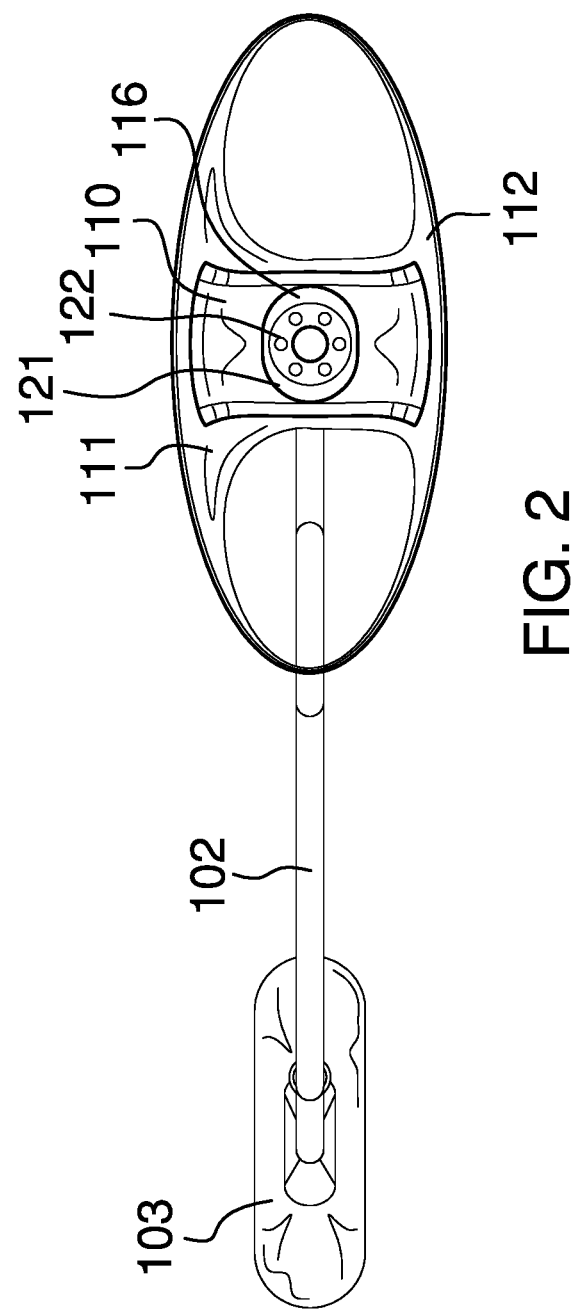
FIG. 2 is a top view of an embodiment of the disclosure.
Figure 3:
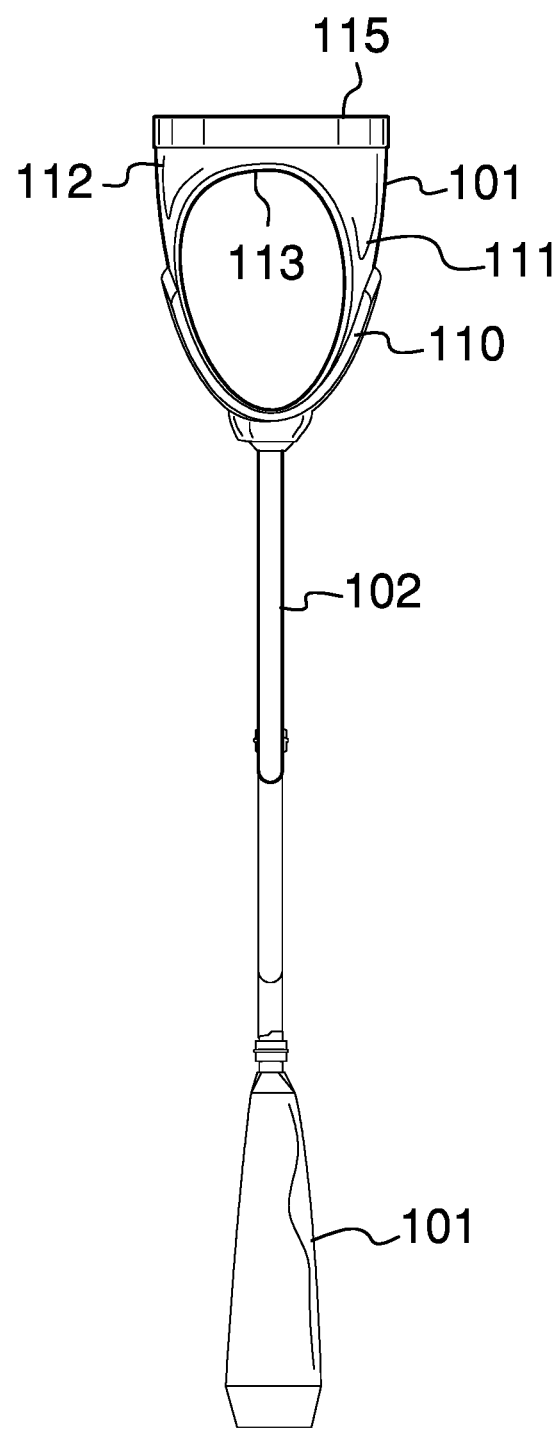
FIG. 3 is a side view of an embodiment of the disclosure.
Figure 4:
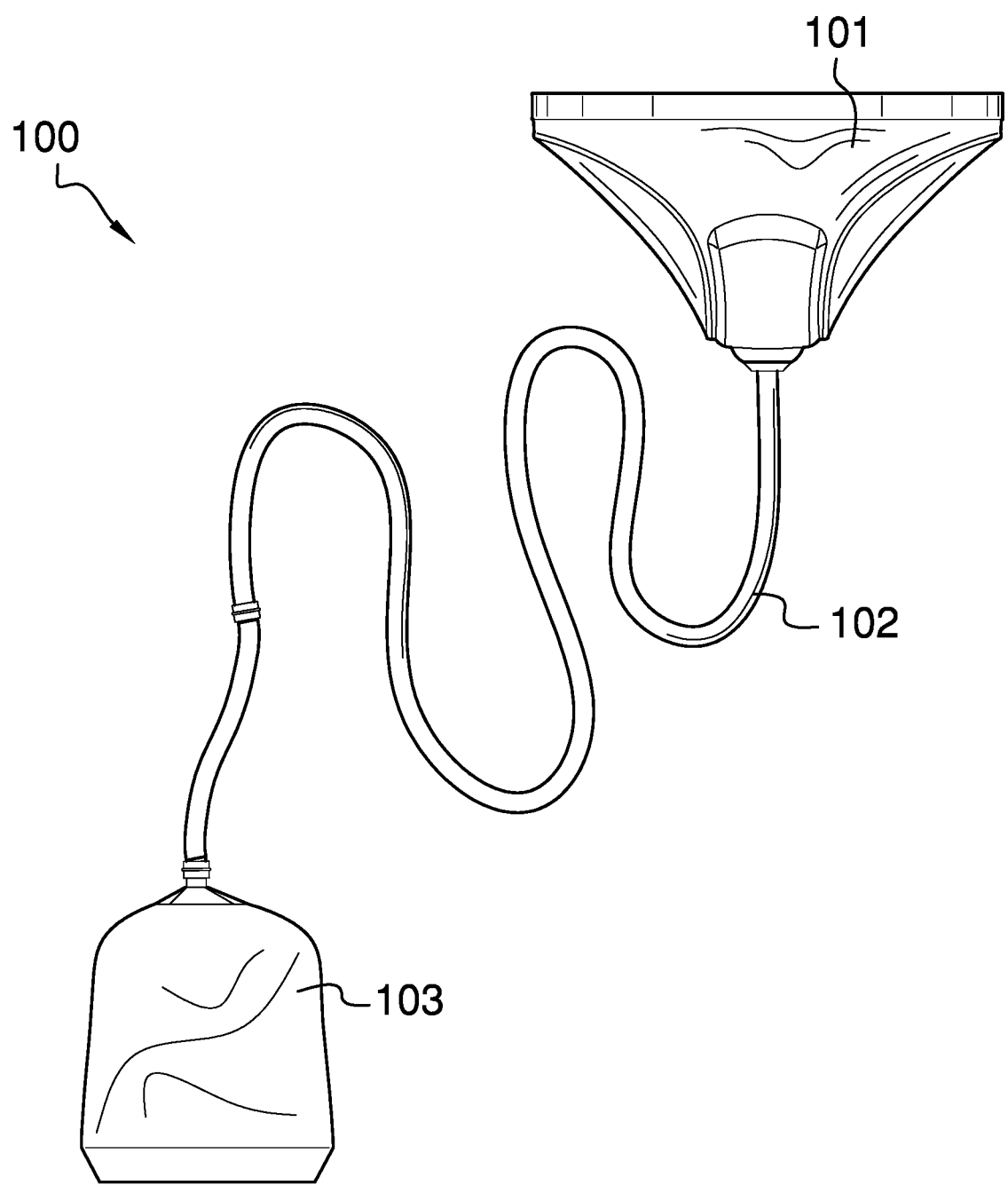
FIG. 4 is a front view of an embodiment of the disclosure.
Figure 5:
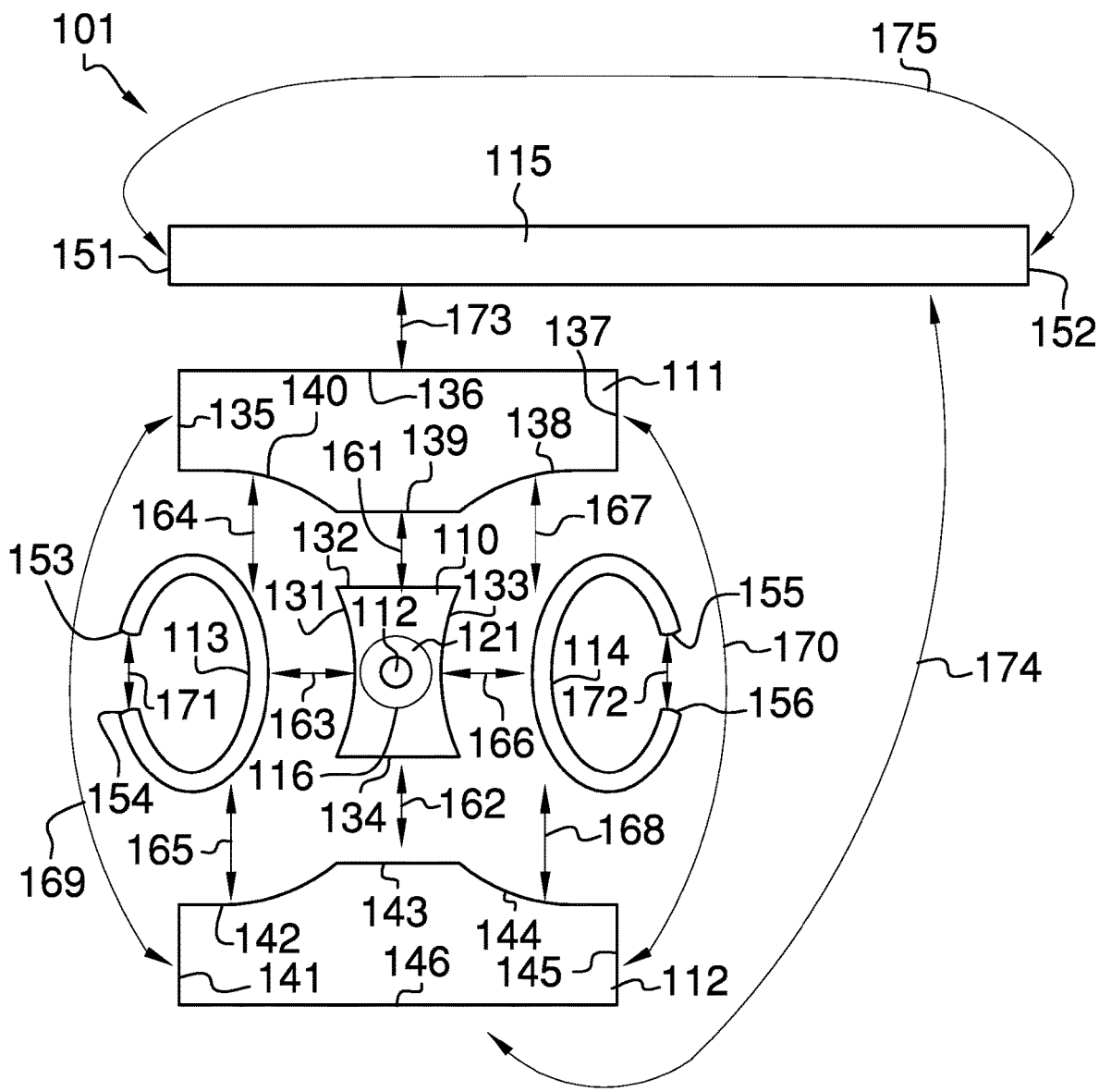
FIG. 5 is a detail view of an embodiment of the disclosure.

Detailed reference will now be made to one or more potential embodiments of the disclosure, which are illustrated in FIGS. 1 through 5.

The undergarment having urine-collection system 100 (hereinafter invention) is an external catheter apparatus. The invention 100 is adapted for use with a patient. The invention 100 is an undergarment 101 that is formed with an elastic sheeting 110. The elastic sheeting 110 is a water impermeable sheeting that collects urine as it is excreted and routes the collected urine to a catheter bag 103. The invention 100 is worn in the same manner as loin wear would be worn. The invention 100 comprises an undergarment 101, a tube 102, and a catheter bag 103. The tube 102 provides a fluidic connection between the undergarment 101 and the catheter bag 103. The tube 102 is a readily and commercially available flexible hose that routes the excreted urine from the undergarment 101 to the catheter bag 103. The tube 102 is further defined with an inner diameter. The catheter bag 103 is a readily and commercially available catheter bag 103 that is used to collect and store the excreted urine for disposal.

The undergarment 101 is an inner garment that is worn underneath outerwear. The undergarment 101 collects the urine excreted by the patient and directs the excreted urine to the drain port 116 where it is collected by the catheter bag 103. The undergarment 101 comprises an elastic sheeting 110, a first panel 111, a second panel 112, a first leg elastic 113, a second leg elastic 114, a waist band 115, and a drain port 116.

The elastic sheeting 110 is a readily and commercially available sheeting. The elastic sheeting 110 is formed from a water impermeable elastomeric material. The elastic sheeting 110 is further defined with a first negative space 123 and a second negative space 124. The elastic sheeting 110 is formed as a rectangular structure that has removed from it the first negative space 123 and the second negative space 124. The elastic sheeting 110 is further defined with a first edge 131, a second edge 132, a third edge 133, and a fourth edge 134. The first negative space 123 is a parabolic structure that forms the boundary of the first edge 131 of the elastic sheeting 110. The purpose of the first negative space 123 is to form a leg hole within the undergarment 101. The second negative space 124 is a parabolic structure that forms the boundary of the third edge 133 of the elastic sheeting 110. The purpose of the second negative space 124 is to form a leg hole within the undergarment 101. The elastic sheeting 110 is formed such that the second edge 132 and the fourth edge 134 are parallel.

The first panel 111 is a textile material that is used to form the undergarment 101. The first panel 111 forms the portion of the undergarment 101 between the elastic sheeting 110 and the waist band 115. The first panel 111 is further defined with a fifth edge 135, a sixth edge 136, a seventh edge 137, an eighth edge 138, a ninth edge 139, and a tenth edge 140.

The first panel 111 is formed such that the fifth edge 135, the sixth edge 136, and the seventh edge 137 form a rectilinear structure with right angles.

The first panel 111 is formed such that the span of the ninth edge 139 equals the span of the second edge 132. The tenth edge 140 is a curved edge that joins the fifth edge 135 to the ninth edge 139. The eighth edge 138 is a curved edge that joins the seventh edge 137 to the ninth edge 139.

The second panel 112 is a textile material that is used to form the undergarment 101. The second panel 112 forms the portion of the undergarment 101 between the elastic sheeting 110 and the waist band 115. The second panel 112 is further defined with an eleventh edge 141, a twelfth edge 142, a thirteenth edge 143, an fourteenth edge 144, a fifteenth edge 145, and a sixteenth edge 146.

The second panel 112 is formed such that the eleventh edge 141, the fifteenth edge 145, and the sixteenth edge 146 form a rectilinear structure with right angles.

The second panel 112 is formed such that the span of the thirteenth edge 143 equals the span of the fourth edge 134. The twelfth edge 142 is a curved edge that joins the eleventh edge 141 to the thirteenth edge 143. The fourteenth edge 144 is a curved edge that joins the fifteenth edge 145 to the thirteenth edge 143.

The first leg elastic 113 is a readily and commercially available elastic webbing that is used to secure the undergarment 101 around the leg of the patient. The first leg elastic 113 is used to form an elastic band. The first leg elastic 113 is further defined with a third end 153 and a fourth end 154.

The second leg elastic 114 is a readily and commercially available elastic webbing that is used to secure the undergarment 101 around the leg of the patient. The second leg elastic 114 is used to form an elastic band. The second leg elastic 114 is further defined with a fifth end 155 and a sixth end 156.

The waist band 115 is a readily and commercially available elastic webbing that is used to secure the undergarment 101 around the waist of the patient. The waist band 115 is used to form an elastic band. The waist band 115 is further defined with a first end 151 and a second end 152.

The drain port 116 is an aperture formed through the elastic sheeting 110 for the purpose of discharging the excreted urine away from the interior surfaces of the undergarment 101. The drain port 116 comprises a grommet 121 and a pipe 122. The pipe 122 is further defined with an outer diameter. The drain port 116 is an aperture formed through the elastic sheeting 110. The drain port 116 is centered on the center of the elastic sheeting 110.

The grommet 121 is a hardware item that provides a water impermeable seal that prevents excreted urine from leaking around the pipe 122 while the invention 100 is in use.

The pipe 122 is a readily and commercially available pipe 122 that forms a stable aperture through which the excreted urine may be discharged. The pipe 122 of the drain port 116 projects away from the exterior surface of the elastic sheeting 110. The span of the outer diameter of the pipe 122 is lesser than the span of the inner diameter of the tube 102 such that the pipe 122 can be inserted into the tube 102. The drain port 116 then attaches to the catheter bag 103 by attaching the other end of the tube 102 to the catheter bag 103 in a normal manner.

The undergarment 101 is assembled as described in following three paragraphs.

The undergarment 101 is assembled with a first seam 161, a second seam 162, a third seam 163, a fourth seam 164, a fifth seam 165, a sixth seam 166, a seventh seam 167, an eighth seam 168, a ninth seam 169, a tenth seam 170, an eleventh seam 171, a twelfth seam 172, a thirteenth seam 173, a fourteenth seam 174, and a fifteenth seam 175.

The first seam 161 attaches the second edge 132 of the elastic sheeting 110 to the ninth edge 139 of the first panel 111. The second seam 162 attaches the fourth edge 134 of the elastic sheeting 110 to the thirteenth edge 143 of the second panel 112. The third seam 163 attaches the first edge 131 of the elastic sheeting 110 to a portion of the center length of the first leg elastic 113. The fourth seam 164 attaches the tenth edge 140 of the first panel 111 to a portion of the center length of the first leg elastic 113. The fifth seam 165 attaches the twelfth edge 142 of the second panel 112 to a portion of the center length of the first leg elastic 113. The sixth seam 166 attaches the third edge 133 of the elastic sheeting 110 to a portion of the center length of the second leg elastic 114. The seventh seam 167 attaches the eighth edge 138 of the first panel 111 to a portion of the center length of the second leg elastic 114. The eighth seam 168 attaches the fourteenth edge 144 of the second panel 112 to a portion of the center length of the second leg elastic 114. The ninth seam 169 attaches the fifth edge 135 of the first panel 111 to the eleventh edge 141 of the second panel 112. The tenth seam 170 attaches the seventh edge 137 of the first panel 111 to the fifteenth edge 145 of the second panel 112. The eleventh seam 171 attaches the third end 153 of the first leg elastic 113 to the fourth end 154 of the first leg elastic 113. The twelfth seam 172 attaches the fifth end 155 of the second leg elastic 114 to the sixth end 156 of the second leg elastic 114. The thirteenth seam 173 attaches the sixth edge 136 of the first panel 111 to a portion of the center length of the waist band 115. The fourteenth seam 174 attaches the sixteenth edge 146 of the second panel 112 to a portion of the center length of the waist band 115. The fifteenth seam 175 attaches the first end 151 of the waist band 115 to the second end 152 of the waist band 115.

In the first potential embodiment of the disclosure, the first seam 161. The first seam 161 is further coated with an epoxy to form a water tight seal at the first seam 161. The second seam 162 is a sewn seam. The second seam 162 is further coated with an epoxy to form a water tight seal at the second seam 162. The third seam 163 is a sewn seam. The third seam 163 is further coated with an epoxy to form a water tight seal at the third seam 163. The fourth seam 164 is a sewn seam. The fifth seam 165 is a sewn seam. The sixth seam 166 is a sewn seam. The sixth seam 166 is further coated with an epoxy to form a water tight seal at the sixth seam 166. The seventh seam 167 is a sewn seam. The eighth seam 168 is a sewn seam. The ninth seam 169 is a sewn seam. The tenth seam 170 is a sewn seam. The eleventh seam 171 is a sewn seam. The twelfth seam 172 is a sewn seam. The thirteenth seam 173 is a sewn seam. The fourteenth seam 174 is a sewn seam. The fifteenth seam 175 is a sewn seam.

The following definitions were used in this disclosure:

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Elastic: As used in this disclosure, an elastic is a material or object that deforms when a force is applied to it and that is able to return to its original shape after the force is removed. A material that exhibits these qualities is also referred to as an elastomeric material.

Elastic Band: As used in this disclosure, an elastic band is a loop of textile that is formed using elastic material that can stretched. Alternatively, the elastic band can be a sheeting that is formed from latex, spandex, or an elastic plastic film that can be stretched.

Elastic Textile: As used in this disclosure, an elastic textile is a textile that contains elastic yarns as some of the yarns that make up the textile. An elastic textile is constructed such that the elastic textile will stretch when a force is applied and will return to its original shape when after the force is removed.

Elastic Webbing: As used in this disclosure, an elastic webbing is a webbing that contains elastic yarns as some of the yarns that make up the webbing. An elastic webbing is constructed such that the elastic webbing will stretch when a force is applied and will return to its original shape when after the force is removed.

Exterior: As used in this disclosure, the exterior is use as a relational term that implies that an object is not contained within the boundary of a structure or a space.

Grommet: As used in this disclosure, a grommet is an eyelet placed in a hole in a textile, sheet, or panel that protects a rope hook or cable passed through it and to protect the textile, sheet, or panel from being torn.

Inner Diameter: As used in this disclosure, the term inner diameter is used in the same way that a plumber would refer to the inner diameter of a pipe.

Interior: As used in this disclosure, the interior is use as a relational term that implies that an object is contained within the boundary of a structure or a space.

Loin Wear: As used in this disclosure, loin wear refers to underclothing that is intended to be worn over the loin region with the occasional exception of the buttocks. Commonly used synonyms for loin wear include, but are not limited to, bikini bottoms, boxer briefs, boxers, briefs, calzones, drawers, French cut, g string, knickers, loincloth, panties, panty, shorts, skivvies, thong, trunks, underpants, undies, and unmentionables.

Loop: As used in this disclosure, a loop is the length of a first linear structure including, but not limited to, lines, cords, or ribbons, that is: 1) folded over and joined at the ends forming an enclosed space; or, 2) curved to form a closed or nearly closed space within the first linear structure. In both cases, the space formed within the first linear structure is such that a second linear structure such as a line, cord or a hook can be inserted through the space formed within the first linear structure. Within this disclosure, the first linear structure is said to be looped around the second linear structure.

Outer Diameter: As used in this disclosure, the term outer diameter is used in the same way that a plumber would refer to the outer diameter of a pipe.

Pipe: As used in this disclosure, a pipe is a hollow cylindrical device that is used for transporting liquids and gases. The line that connects the center of the first base of the cylinder to the center of the second base of the cylinder is referred to as the axis of the cylinder or the centerline of the pipe. When two pipes share the same centerline they are said to be aligned. In this disclosure, the terms inner diameter of a pipe and outer diameter are used as they would be used by those skilled in the plumbing arts.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Sheeting: As used in this disclosure, sheeting is a material, such as a textile, a plastic, or a metal foil, in the form of a thin flexible layer or layers.

Textile: As used in this disclosure, a textile is a material that is woven, knitted, braided or felted. Synonyms in common usage for this definition include fabric and cloth.

Tube: As used in this disclosure, a tube is a flexible hollow cylindrical device that is used for transporting liquids and gases. The line that connects the center of the first base of the cylinder to the center of the second base of the cylinder is referred to as the center axis of the tube or the centerline of the tube. In this disclosure, the terms inner dimension of a tube and outer dimension of a tube are used as they would be used by those skilled in the plumbing arts.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A medical device comprising:
   wherein the medical device comprises an undergarment, a tube, and a catheter bag;
   wherein the tube provides a fluidic connection between the undergarment and the catheter bag;
   wherein the medical device is an undergarment;
   wherein the undergarment collects urine as it is excreted and routes the collected urine to the catheter bag;
   wherein the tube is a flexible hose that routes the excreted urine from the undergarment to the catheter bag;
   wherein the tube is further defined with an inner diameter;
   wherein the undergarment is an inner garment;
   wherein the undergarment comprises an elastic sheeting, a first panel, a second panel, a first leg elastic, a second leg elastic, a waist band, and a drain port;
   wherein the elastic sheeting, the first panel, the second panel, the first leg elastic, the second leg elastic, the waist band, and the drain port are attached to each other to form the garment;
   wherein the elastic sheeting is a sheeting formed from a water impermeable elastomeric material;
   wherein the elastic sheeting is further defined with a first negative space and a second negative space;
   wherein the elastic sheeting is formed as a rectangular structure that has removed from it the first negative space and the second negative space;
   wherein the elastic sheeting is further defined with a first edge, a second edge, a third edge, and a fourth edge;
   wherein the first negative space is a parabolic structure that forms the boundary of the first edge of the elastic sheeting;
   wherein the second negative space is a parabolic structure that forms the boundary of the third edge of the elastic sheeting;
   wherein the elastic sheeting is formed such that the second edge and the fourth edge are parallel;
   wherein the first panel is a textile material;
   wherein the first panel forms the portion of the undergarment between the elastic sheeting and the waist band;
   wherein the first panel is further defined with a fifth edge, a sixth edge, a seventh edge, an eighth edge, a ninth edge, and a tenth edge;
   wherein the first panel is formed such that the fifth edge, the sixth edge, and the seventh edge form a first rectilinear structure with right angles;
   wherein the first panel is formed such that the span of the ninth edge equals the span of the second edge;
   wherein the tenth edge is a curved edge that joins the fifth edge to the ninth edge;
   wherein the eighth edge is a curved edge that joins the seventh edge to the ninth edge.

2. The medical device according to claim 1
   wherein the second panel is a textile material;
   wherein the second panel forms the portion of the undergarment between the elastic sheeting and the waist band;
   wherein the second panel is further defined with an eleventh edge, a twelfth edge, a thirteenth edge, a fourteenth edge, a fifteenth edge, and a sixteenth edge;
   wherein the second panel is formed such that the eleventh edge, the fifteenth edge, and the sixteenth edge form a second rectilinear structure with right angles;
   wherein the second panel is formed such that the span of the thirteenth edge equals the span of the fourth edge;
   wherein the twelfth edge is a curved edge that joins the eleventh edge to the thirteenth edge;
   wherein the fourteenth edge is a curved edge that joins the fifteenth edge to the thirteenth edge.

3. The medical device according to claim 2
   wherein the first leg elastic is a first elastic webbing;
   wherein the first leg elastic secures the undergarment to a leg of the patient;
   wherein the first leg elastic forms an elastic band;
   wherein the first leg elastic is further defined with a third end and a fourth end.

4. The medical device according to claim 3
   wherein the second leg elastic is a second elastic webbing;
   wherein the second leg elastic secures the undergarment to a leg of the patient;
   wherein the second leg elastic forms an elastic band;
   wherein the second leg elastic is further defined with a third end and a fourth end.

5. The medical device according to claim 4
   wherein the waist band is a third elastic webbing;
   wherein the waist band secures the undergarment to a waist of the patient;
   wherein the waist band is used to form an elastic band;
   wherein the waist band is further defined with a first end and a second end.

6. The medical device according to claim 5
   wherein the drain port is an aperture formed through the elastic sheeting;
   wherein the drain port comprises a grommet and a pipe;
   wherein the pipe is further defined with an outer diameter;
   wherein the drain port is centered on the center of the elastic sheeting;
   wherein the pipe forms a stable aperture through which the excreted urine is discharged;
   wherein the grommet provides a water impermeable seal around the pipe.

7. The medical device according to claim 6
   wherein the pipe of the drain port projects away from the exterior surface of the elastic sheeting;
   wherein the span of the outer diameter of the pipe is lesser than the span of the inner diameter of the tube such that the pipe can be inserted into the tube.

8. The medical device according to claim 7 wherein the undergarment is assembled with a first seam, a second seam, a third seam, a fourth seam, a fifth seam, a sixth seam, a seventh seam, an eighth seam, a ninth seam, a tenth seam, an eleventh seam, a twelfth seam, a thirteenth seam, a fourteenth seam, and a fifteenth seam.

9. The medical device according to claim 8
   wherein the first seam attaches the second edge of the elastic sheeting to the ninth edge of the first panel;
   wherein the second seam attaches the fourth edge of the elastic sheeting to the thirteenth edge of the second panel;
   wherein the third seam attaches the first edge of the elastic sheeting to a portion of the center length of the first leg elastic;
   wherein the fourth seam attaches the tenth edge of the first panel to a portion of the center length of the first leg elastic;
   wherein the fifth seam attaches the twelfth edge of the second panel to a portion of the center length of the first leg elastic;
   wherein the sixth seam attaches the third edge of the elastic sheeting to a portion of the center length of the second leg elastic;
   wherein the seventh seam attaches the eighth edge of the first panel to a portion of the center length of the second leg elastic;

wherein the eighth seam attaches the fourteenth edge of the second panel to a portion of the center length of the second leg elastic;
wherein the ninth seam attaches the fifth edge of the first panel to the eleventh edge of the second panel;
wherein the tenth seam attaches the seventh edge of the first panel to the fifteenth edge of the second panel;
wherein the eleventh seam attaches the third end of the first leg elastic to the fourth end of the first leg elastic;
wherein the twelfth seam attaches the fifth end of the second leg elastic to the sixth end of the second leg elastic;
wherein the thirteenth seam attaches the sixth edge of the first panel to a portion of the center length of the waist band;
wherein the fourteenth seam attaches the sixteenth edge of the second panel to a portion of the center length of the waist band;
wherein the fifteenth seam attaches the first end of the waist band to the second end of the waist band.

10. The medical device according to claim 9
wherein the first seam is further coated with an epoxy to form a water tight seal at the first seam;
wherein the second seam is further coated with an epoxy to form a water tight seal at the second seam;
wherein the third seam is further coated with an epoxy to form a water tight seal at the third seam;
wherein the sixth seam is further coated with an epoxy to form a water tight seal at the sixth seam.

11. The medical device according to claim 10
wherein the first seam is a sewn seam;
wherein the second seam is a sewn seam;
wherein the third seam is a sewn seam;
wherein the fourth seam is a sewn seam;
wherein the fifth seam is a sewn seam;
wherein the sixth seam is a sewn seam;
wherein the seventh seam is a sewn seam;
wherein the eighth seam is a sewn seam;
wherein the ninth seam is a sewn seam;
wherein the tenth seam is a sewn seam;
wherein the eleventh seam is a sewn seam;
wherein the twelfth seam is a sewn seam;
wherein the thirteenth seam is a sewn seam;
wherein the fourteenth seam is a sewn seam;
wherein the fifteenth seam is a sewn seam.

12. The medical device according to claim 1
wherein the drain port is an aperture formed through the elastic sheeting;
wherein the drain port comprises a grommet and a pipe;
wherein the pipe is further defined with an outer diameter;
wherein the drain port is centered on the center of the elastic sheeting;
wherein the pipe forms a stable aperture through which the excreted urine is discharged;
wherein the grommet provides a water impermeable seal around the pipe;
wherein the pipe of the drain port projects away from the exterior surface of the elastic sheeting;
wherein the span of the outer diameter of the pipe is lesser than the span of the inner diameter of the tube such that the pipe can be inserted into the tube.

13. The medical device according to claim 12
wherein the first panel is a textile material;
wherein the first panel forms the portion of the undergarment between the elastic sheeting and the waist band;
wherein the first panel is further defined with a fifth edge, a sixth edge, a seventh edge, an eighth edge, a ninth edge, and a tenth edge;
wherein the first panel is formed such that the fifth edge, the sixth edge, and the seventh edge form a first rectilinear structure with right angles;
wherein the first panel is formed such that the span of the ninth edge equals the span of the second edge;
wherein the tenth edge is a curved edge that joins the fifth edge to the ninth edge;
wherein the eighth edge is a curved edge that joins the seventh edge to the ninth edge;
wherein the second panel is a textile material;
wherein the second panel forms the portion of the undergarment between the elastic sheeting and the waist band;
wherein the second panel is further defined with an eleventh edge, a twelfth edge, a thirteenth edge, a fourteenth edge, a fifteenth edge, and a sixteenth edge;
wherein the second panel is formed such that the eleventh edge, the fifteenth edge, and the sixteenth edge form a second rectilinear structure with right angles;
wherein the second panel is formed such that the span of the thirteenth edge equals the span of the fourth edge;
wherein the twelfth edge is a curved edge that joins the eleventh edge to the thirteenth edge;
wherein the fourteenth edge is a curved edge that joins the fifteenth edge to the thirteenth edge.

14. The medical device according to claim 13
wherein the first leg elastic is a first elastic webbing;
wherein the first leg elastic secures the undergarment to a leg of the patient;
wherein the first leg elastic forms an elastic band;
wherein the first leg elastic is further defined with a third end and a fourth end;
wherein the second leg elastic is a second elastic webbing;
wherein the second leg elastic secures the undergarment to a leg of the patient;
wherein the second leg elastic forms an elastic band;
wherein the second leg elastic is further defined with a third end and a fourth end;
wherein the waist band is a third elastic webbing;
wherein the waist band secures the undergarment to a waist of the patient;
wherein the waist band is used to form an elastic band;
wherein the waist band is further defined with a first end and a second end.

15. The medical device according to claim 14
wherein the undergarment is assembled with a first seam, a second seam, a third seam, a fourth seam, a fifth seam, a sixth seam, a seventh seam, an eighth seam, a ninth seam, a tenth seam, an eleventh seam, a twelfth seam, a thirteenth seam, a fourteenth seam, and a fifteenth seam;
wherein the first seam is a sewn seam;
wherein the second seam is a sewn seam;
wherein the third seam is a sewn seam;
wherein the fourth seam is a sewn seam;
wherein the fifth seam is a sewn seam;
wherein the sixth seam is a sewn seam;
wherein the seventh seam is a sewn seam;
wherein the eighth seam is a sewn seam;
wherein the ninth seam is a sewn seam;
wherein the tenth seam is a sewn seam;
wherein the eleventh seam is a sewn seam;
wherein the twelfth seam is a sewn seam;
wherein the thirteenth seam is a sewn seam;

wherein the fourteenth seam is a sewn seam;
wherein the fifteenth seam is a sewn seam.

16. The medical device according to claim 15
wherein the first seam attaches the second edge of the elastic sheeting to the ninth edge of the first panel;
wherein the second seam attaches the fourth edge of the elastic sheeting to the thirteenth edge of the second panel;
wherein the third seam attaches the first edge of the elastic sheeting to a portion of the center length of the first leg elastic;
wherein the fourth seam attaches the tenth edge of the first panel to a portion of the center length of the first leg elastic;
wherein the fifth seam attaches the twelfth edge of the second panel to a portion of the center length of the first leg elastic;
wherein the sixth seam attaches the third edge of the elastic sheeting to a portion of the center length of the second leg elastic;
wherein the seventh seam attaches the eighth edge of the first panel to a portion of the center length of the second leg elastic;
wherein the eighth seam attaches the fourteenth edge of the second panel to a portion of the center length of the second leg elastic;
wherein the ninth seam attaches the fifth edge of the first panel to the eleventh edge of the second panel;
wherein the tenth seam attaches the seventh edge of the first panel to the fifteenth edge of the second panel;
wherein the eleventh seam attaches the third end of the first leg elastic to the fourth end of the first leg elastic;
wherein the twelfth seam attaches the fifth end of the second leg elastic to the sixth end of the second leg elastic;
wherein the thirteenth seam attaches the sixth edge of the first panel to a portion of the center length of the waist band;
wherein the fourteenth seam attaches the sixteenth edge of the second panel to a portion of the center length of the waist band;
wherein the fifteenth seam attaches the first end of the waist band to the second end of the waist band.

17. The medical device according to claim 16
wherein the first seam is further coated with an epoxy;
wherein the second seam is further coated with an epoxy;
wherein the third seam is further coated with an epoxy;
wherein the sixth seam is further coated with an epoxy.

* * * * *